United States Patent
Romano

[11] Patent Number: 5,942,759
[45] Date of Patent: Aug. 24, 1999

[54] COUNTERFEIT DETECTION VIEWER APPARATUS HAVING A REMOVABLE COUNTERFEIT DETECTOR UNIT FOR PAPER CURRENCY

[76] Inventor: Camille Romano, 7436 SW. 117th Ave., Suite 208, Miami, Fla. 33183

[21] Appl. No.: 08/999,105

[22] Filed: Dec. 29, 1997

Related U.S. Application Data

[63] Continuation-in-part of application No. 08/772,811, Dec. 24, 1996, Pat. No. 5,874,742.

[51] Int. Cl.⁶ .................................................. G01N 21/64
[52] U.S. Cl. .................................... 250/461.1; 250/504 H
[58] Field of Search ............................ 250/458.1, 461.1, 250/485.1, 504 H, 504 R

[56] References Cited

U.S. PATENT DOCUMENTS

| | | | |
|---|---|---|---|
| 3,618,765 | 11/1971 | Cooper et al. | 209/534 |
| 3,774,046 | 11/1973 | Hoch et al. | 250/485.1 |
| 3,842,281 | 10/1974 | Goodrich | 250/485.1 |
| 4,558,224 | 12/1985 | Gober | 250/461.1 |
| 5,444,263 | 8/1995 | Mastnak | 250/504 H |
| 5,572,319 | 11/1996 | Blackman et al. | 356/238 |
| 5,668,377 | 9/1997 | Erickson | 250/504 R |

Primary Examiner—Constantine Hannaher
Assistant Examiner—Darren M. Jiron
Attorney, Agent, or Firm—Ezra Sutton

[57] ABSTRACT

A counterfeit detection viewer apparatus for detecting security markings in paper currency. The counterfeit detection viewer apparatus includes a viewer housing having a detection opening on the bottom thereof for receiving the paper currency to be inspected and a viewing opening on the top thereof for inspecting the paper currency. The counterfeit detection viewer apparatus further includes a pair of holding brackets for detachably holding the counterfeit detector unit within the viewer housing which is usable within the housing and is removable for use as a hand-held counterfeit detector unit in a dark room or dark area. The counterfeit detector unit includes a UV light fixture mounted in the counterfeit detector unit having a UV fluorescent lamp for projecting UV light rays toward the detection opening and the paper currency to be inspected. The UV fluorescent lamp being less than 0.5 cm from the detection opening. The counterfeit detector unit further includes a movable cover for protecting the UV fluorescent lamp when not in use. In addition, the counterfeit detector unit includes a battery compartment for receiving batteries to power the UV fluorescent lamp; and an ON/OFF switch for activating said UV fluorescent lamp prior to inspecting the paper currency through the viewing opening.

30 Claims, 7 Drawing Sheets

COUNTERFEIT DETECTION VIEWER APPARATUS HAVING A REMOVABLE COUNTERFEIT DETECTOR UNIT FOR PAPER CURRENCY

This is a continuation-in-part of application Ser. No. 08/772,811, filed on Dec. 24, 1996, now U.S. Pat. No. 5,874,742.

FIELD OF INVENTION

This invention relates to an improved counterfeit detection viewer apparatus having a removable portable counterfeit detector hand-held unit for the detection of counterfeit paper currency. More particularly, it relates to a viewer apparatus and hand-held unit for identifying instantaneously the security markings of valid paper currency by using ultra violet fluorescent lighting.

BACKGROUND OF THE INVENTION

It is well known that ever since paper currency was developed and put into use, the governments throughout the world have been concerned with the problem of counterfeiting. As duplicating and printing, and especially color photocopying techniques have advanced over the years, it is more difficult than ever to distinguish between counterfeit and legitimate paper currency. It is obvious that the problem of counterfeiting paper currency is and has been a major concern of many governments, banks, commercial businesses and retail stores around the world.

In response to the challenge of the ever growing concern of counterfeiting, various instruments and detectors have been developed for detecting counterfeit currency. However, it has been discovered that known instruments and detectors are not reliable, or are too expensive to manufacture. In some cases such instruments are too bulky and/or complex in design.

In addition, recently new U.S. currency has been developed to include new security features including a polymer thread which has fluorescent markings sensitive to ultra violet light and which are barely visible in ambient lighting conditions. However, under intensified ultra violet fluorescent lighting, the polymer thread glows a particular color for each denomination (red for U.S. $100 bill, yellow for U.S. $50 bill, etc.) to indicate that the currency is authentic.

There remains a need for a counterfeit detection viewer apparatus that instantaneously authenticates and validates the security markings of U.S. paper currency, foreign currency and essential governmental documents. In addition, the counterfeit detection viewer apparatus should have a removable portable counterfeit detector hand-held unit that is lightweight, durable, battery-operated and convenient to use. Also, the apparatus should provide a counterfeit detection system and methodology for the duplicate checking of counterfeit currency or governmental documents.

DESCRIPTION OF THE PRIOR ART

Counterfeit detection instruments, counterfeit detection apparatus and the like having various designs, structure, configurations and materials of construction have been disclosed in the prior art. For example, U.S. Pat. No. 3,618,765 to Cooper et al discloses a counterfeit currency detector having a housing and light sources. The light sources are long-wave ultraviolet light bulbs with an integral filter or exterior filter to absorb most visible light and transmit the desired ultraviolet rays. The light sources are located in the upper surface area of the housing, which has an opening to facilitate positioning of the paper currency below the filter, such that the currency is exposed to the UV light sources. This prior art patent does not disclose the design, structure and configuration of the present invention.

U.S. Pat. Nos. 3,725,694; 3,774,046; and 4,558,224 all disclose counterfeit currency detectors having a housing unit and a UV light source with an internal bill receptor for exposing the bill to the UV light source. None of these aforementioned prior art patents disclose the design, structure and configuration of the present invention.

U.S. Pat. No. 5,572,319 to Blackman et al discloses a stain detector apparatus. The detector apparatus includes a housing having an incandescent lamp and fluorescent lamp for projecting light rays towards a fabric opening for inspecting the fabric for stains. This prior art patent does not disclose the design, structure and configuration of the present invention.

Japanese Patent No. 63-298140 to Horaguchi et al discloses an apparatus for checking stains and contamination. The apparatus includes an UV lamp housed within a black box. This prior art patent does not disclose the design, structure and configuration of the present invention.

These prior art patents do not disclose or teach the use of an instrument for instantaneous detection of counterfeit currency or false documents having the design and configuration of the present invention.

Accordingly, it is an object of the present invention to provide counterfeit detection viewer apparatus that allows for instantaneous detection of security markings of valid and authentic paper currency, or showing the lack of proper security markings of counterfeit paper currency.

Another object of the present invention is to provide a counterfeit detection viewer apparatus for instantly detecting the security markings and verifying the validity and authenticity of any essential documents that include passports, entry visas, immigration green cards, driving licenses, vehicle registrations, credit cards, travelers checks, or other foreign currencies.

Another object of the present invention is to provide a counterfeit detection viewer apparatus for instantly detecting counterfeit paper currency by providing a housing to intensify UV fluorescent light from a fluorescent lamp, even under normal ambient bright lighting conditions.

Another object of the present invention is to provide a counterfeit detection viewer apparatus having a detachable counterfeit detector hand-held unit that is easy to use, portable, convenient and durable.

Another object of the present invention is to provide a counterfeit detection viewer apparatus having a detachable counterfeit detector unit that is portable, battery-operated, lightweight, compact and hand held.

Another object of the present invention is to provide a detachable counterfeit detector unit having a black rotary cover that can be turned and rotated halfway over to become a shield protecting the lower half of the UV fluorescent tube from ambient light during operational use.

Another object of the present invention is to provide a detachable counterfeit detector unit having a black rotary cover, such that when the cover is completely closed (100% rotation), the cover will disconnect the batteries and will also protect the UV fluorescent tube from breakage when the detachable counterfeit detector unit is carried in a user's pocket, purse, knap-sack, carrying case or attache case.

Another object of the present invention is to provide a counterfeit detection viewer apparatus having exterior storage compartments for pen-type chemical markers that include a counterfeit chemical detector for detecting counterfeit paper currency and a fluorescent marker for identification of valuables under UV lighting.

A further object of the present invention is to provide a counterfeit detection viewer apparatus that can be mass produced in an automated and economical manner and is readily affordable by the user.

SUMMARY OF THE INVENTION

In accordance with the present invention, there is provided a counterfeit detection viewer apparatus for detecting security markings in paper currency. The counterfeit detection viewer apparatus includes a viewer housing having a detection opening on the bottom thereof for receiving the paper currency to be inspected and a viewing opening on the top thereof for inspecting the paper currency. The counterfeit detection viewer apparatus further includes a pair of holding brackets for detachably holding a counterfeit detector unit within the viewer housing which is usable within the housing and is removable for use as a hand-held counterfeit detector unit in a dark room or dark area. The counterfeit detector unit includes a UV light fixture mounted in the counterfeit detector unit having a UV fluorescent lamp for projecting UV light rays toward the detection opening and the paper currency to be inspected; the UV fluorescent lamp being less than 0.5 centimeters from the detection opening. The counterfeit detector unit further includes a movable cover for protecting the UV fluorescent lamp when not in use. In addition, the counterfeit detector unit includes a battery compartment for receiving batteries to power the UV fluorescent lamp; and an ON/OFF switch for activating said UV fluorescent lamp prior to inspecting the paper currency through the viewing opening.

BRIEF DESCRIPTION OF DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

Figure 1:
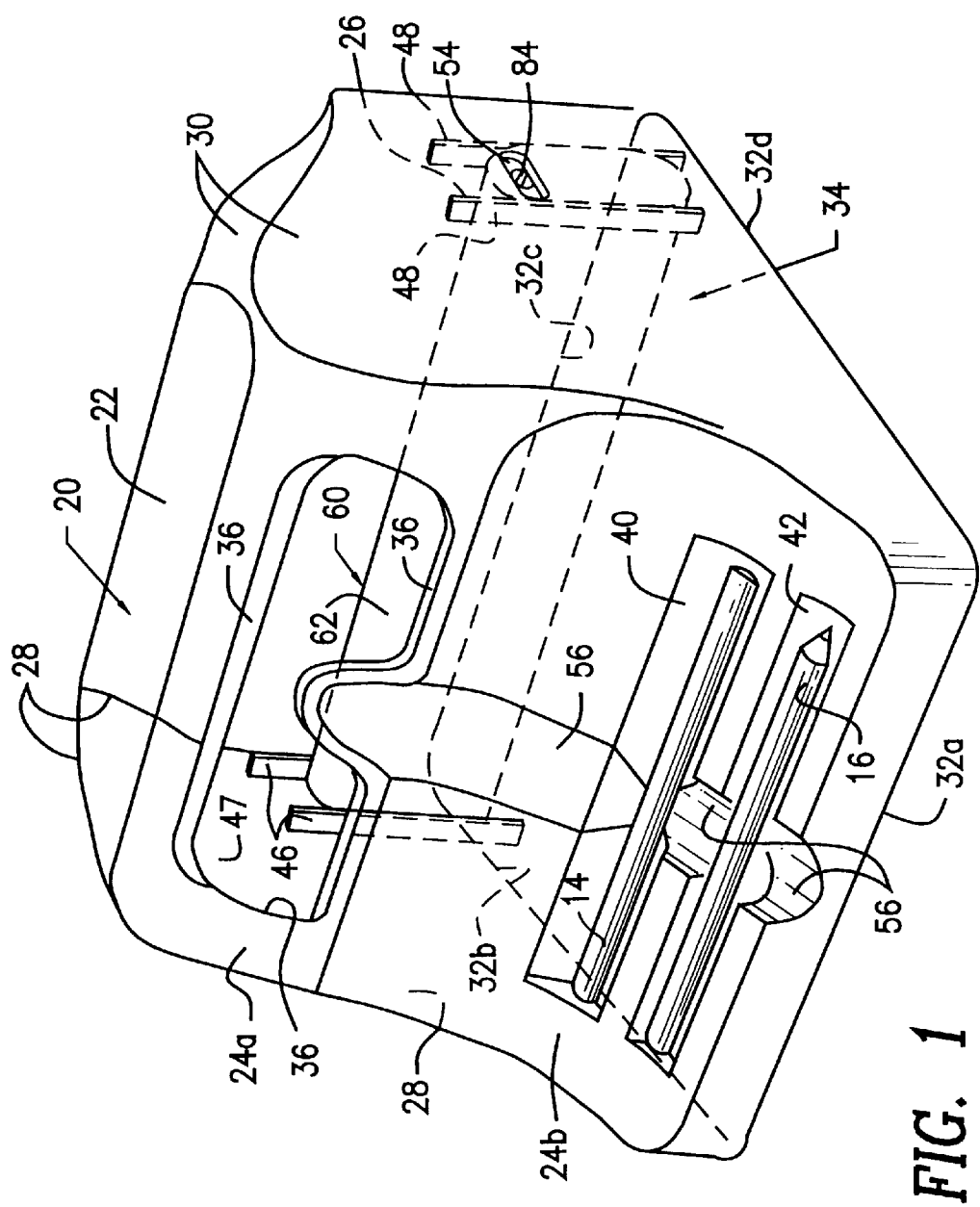
FIG. 1 is a front perspective view of the counterfeit detection viewer apparatus of the preferred embodiment of the present invention showing the major component parts contained therein.
Figure 2:
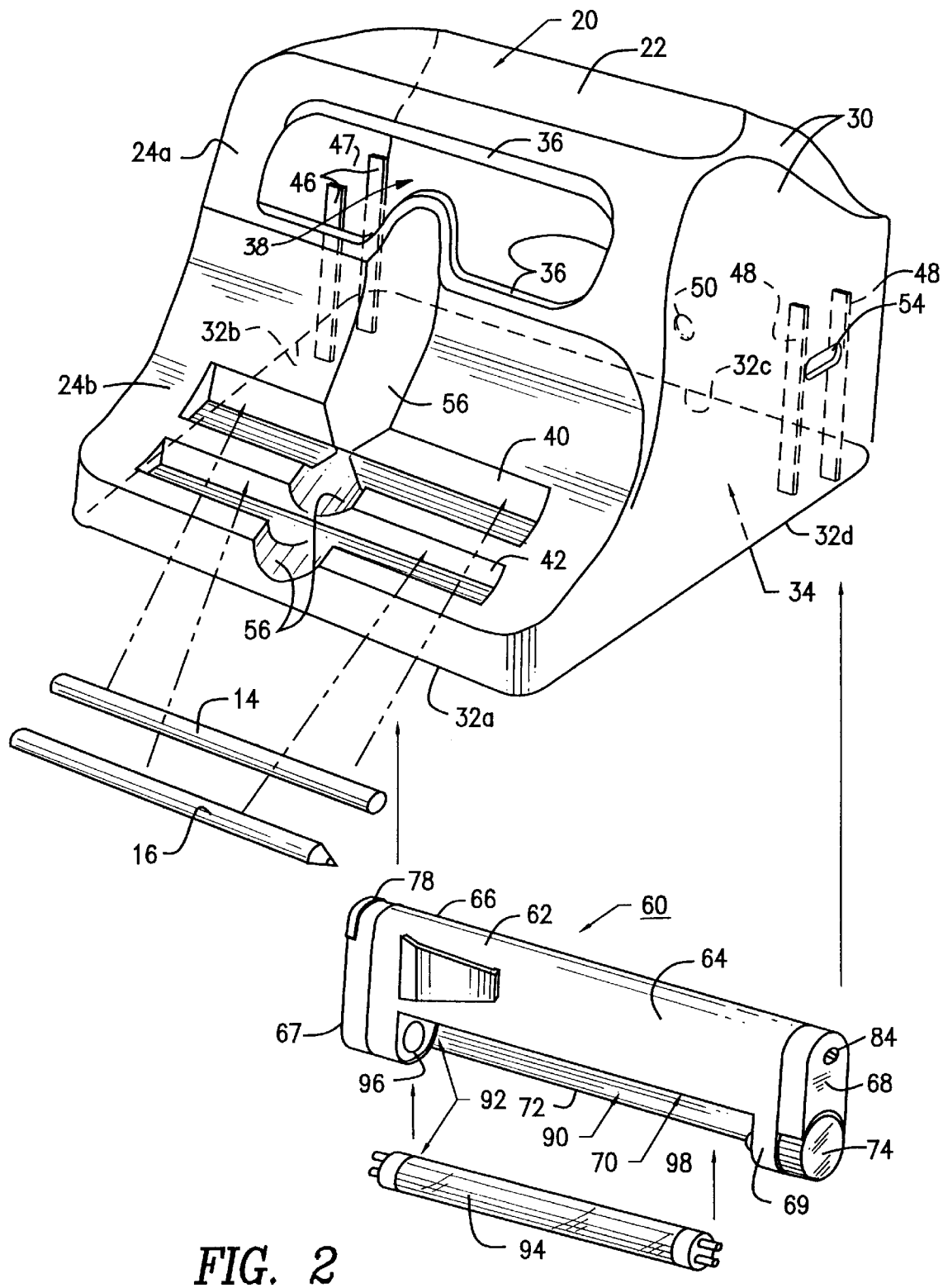
FIG. 2 is a front exploded perspective view of the counterfeit detection viewer apparatus of the preferred embodiment of the present invention showing the major component parts contained therein, and in operational use.
Figure 3:
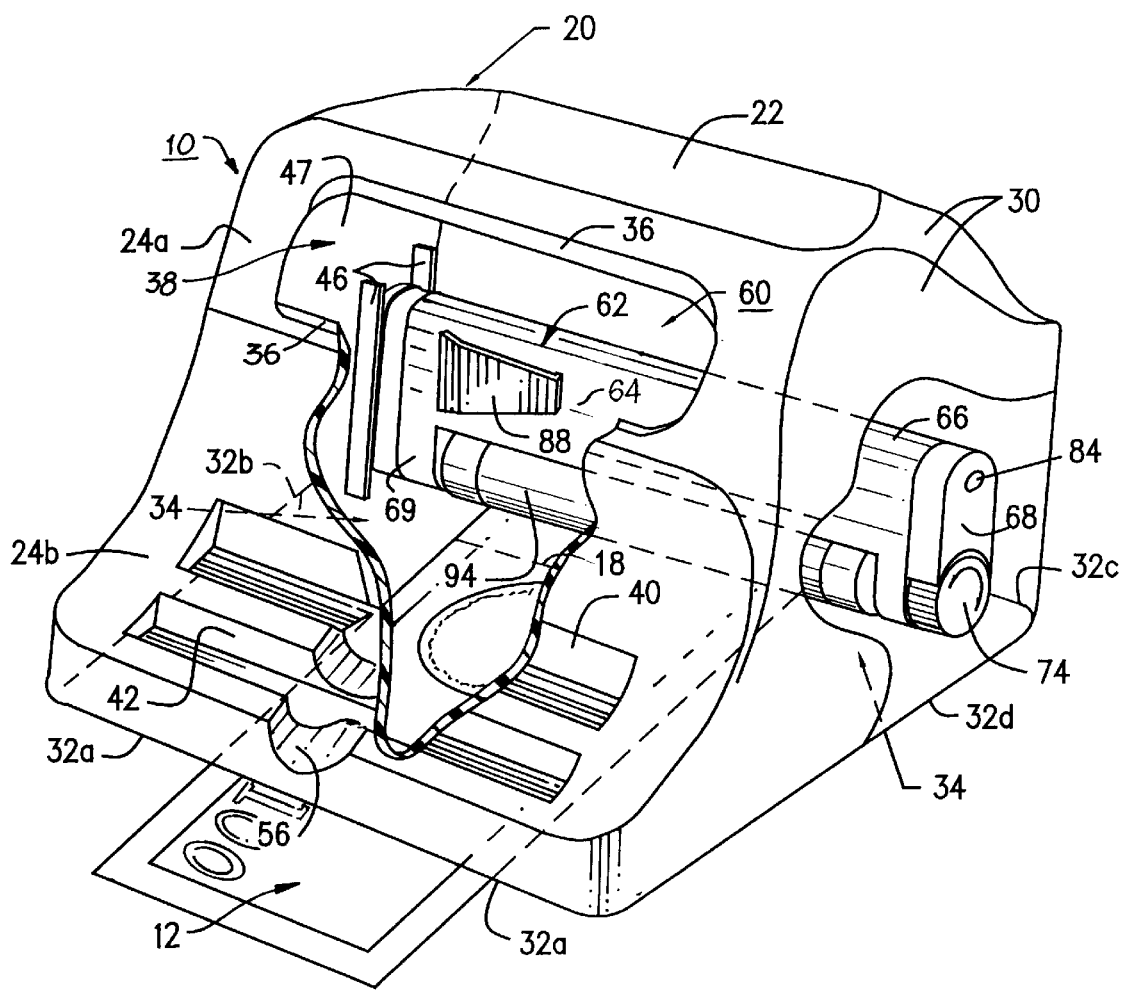
FIG. 3 is a front perspective view of the counterfeit detection viewer apparatus of the preferred embodiment of the present invention showing the major component parts contained therein, and in operational use.
Figure 4:
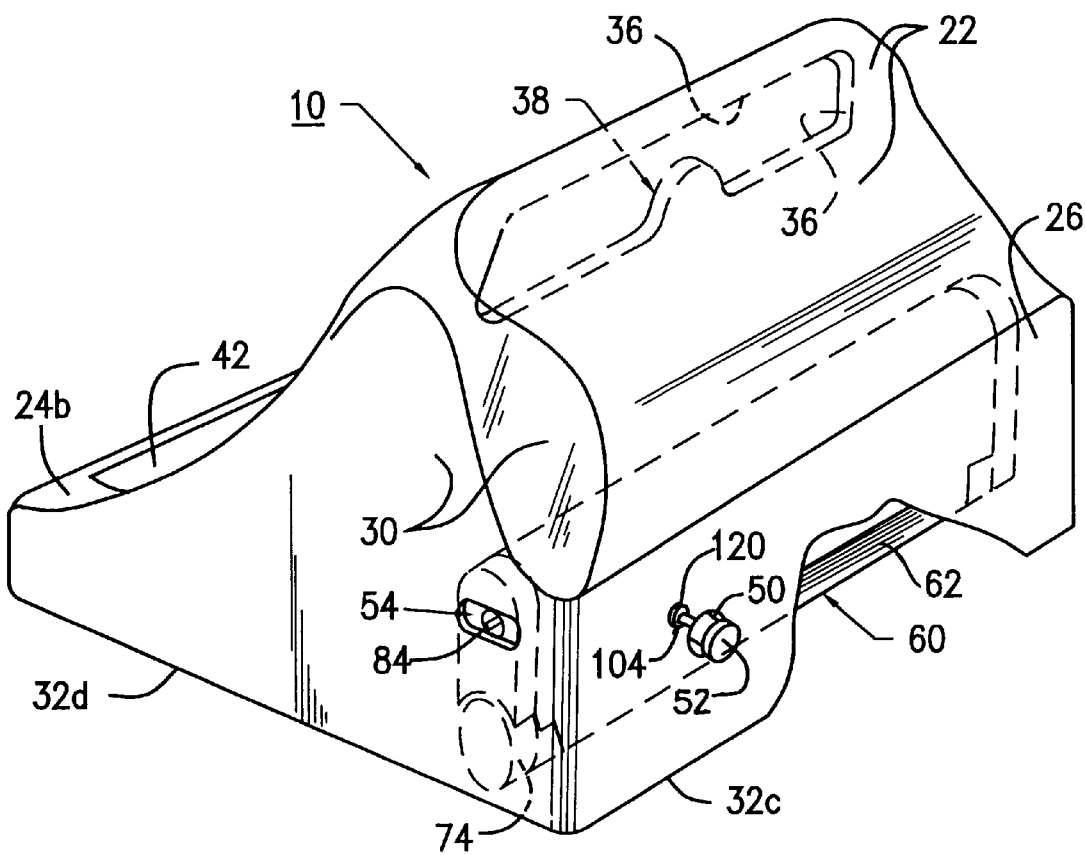
FIG. 4 is a rear perspective view of the counterfeit detection viewer apparatus of the preferred embodiment of the present invention showing the ON/OFF button on the rear wall and the AC adaptor connector opening on the side wall of the apparatus housing.
Figure 5:
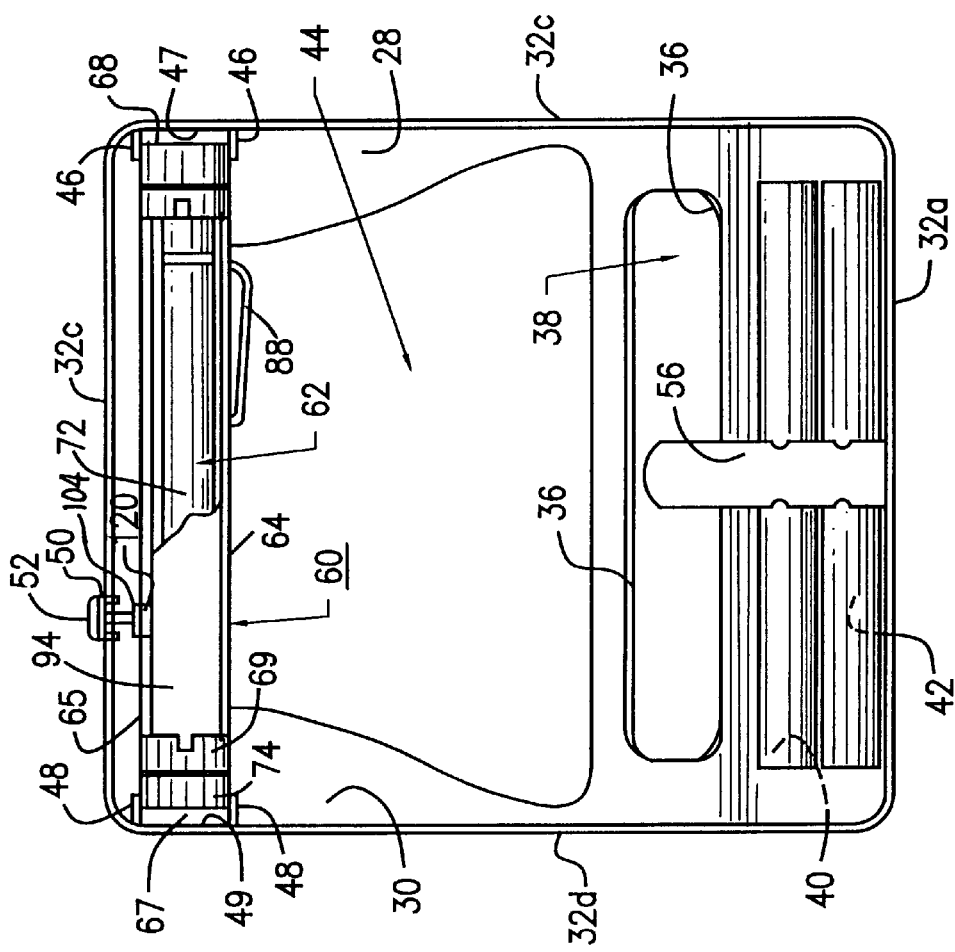
FIG. 5 is a bottom plan view of the counterfeit detection viewer apparatus of the preferred embodiment of the present invention showing the detection opening, the viewing opening, and the UV fluorescent tube with miniature sockets.
Figure 6:
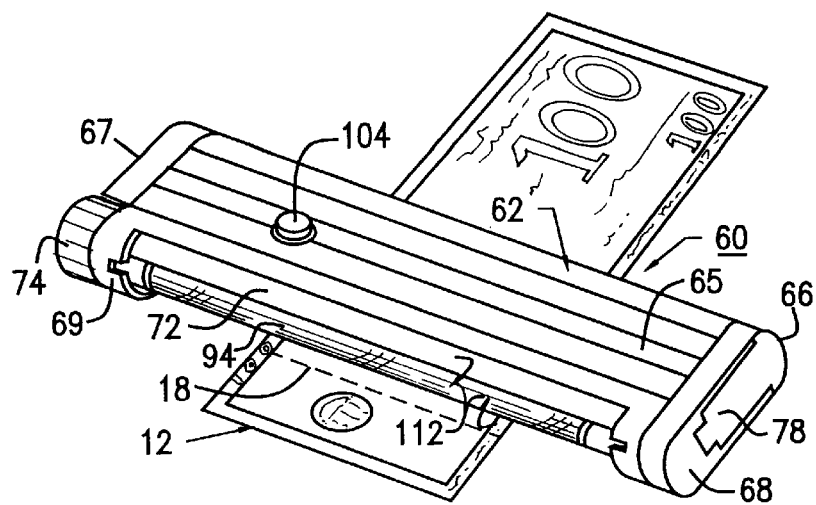
FIG. 6 is a rear perspective view of the counterfeit detection viewer apparatus of the present invention showing the removable portable counterfeit detector handset having the internal UV lighting assembly and its major component parts contained therein, and in operational use where the rotary cover is halfway (50%) rotated for shielding the UV fluorescent tube from ambient light.

The portable desktop/countertop counterfeit detection viewer apparatus 10 and its component parts of the preferred embodiment of the present invention are represented in detail by FIGS. 1 to 9. The counterfeit detection viewer apparatus 10 includes a viewer housing 20 having a substantially rectangular configuration for holding a removable portable hand-held unit 60 having an internal battery compartment 76 for batteries 82 and having an internal UV lighting assembly 90. The internal UV lighting assembly 90, as shown in FIG. 2, includes a UV lighting fixture 92 using a UV fluorescent tube 94 for detecting the security marking 18 of an authentic paper currency 12. As shown in FIG. 3, the counterfeit detection viewer apparatus 10 is in an operational mode for detecting the security marking 18 in order to detect a counterfeit currency bill from a valid and authentic currency bill. As shown in FIG. 6, the hand-held portable counterfeit detector unit 60 is in an operational mode for detecting the security marking 18 in order to detect a counterfeit currency bill from a valid and authentic currency bill.

Viewer housing 20, as shown in FIGS. 1, 2 and 4, includes a top wall section 22, an upper front wall section 24a, a lower front wall section 24b, a rear wall section 26 and side wall sections 28 and 30, all being integrally connected to form a substantially rectangular shaped configuration which forms an interior compartment 44. As shown in FIG. 5, housing 20 further includes bottom perimeter edges 32a, 32b, 32c and 32d which define a detection opening 34 on the bottom of housing 20. Interior compartment 44 includes a pair of holding brackets 46 and 48 for detachably receiving and holding the removable portable counterfeit detection handset or counterfeit detector unit 60. Holding brackets 46 and 48 are located on the interior sidewall surfaces 47 and 49, respectively, as shown in FIGS. 2 and 5 of the drawings. Viewer housing 20 also includes an upper rectangular perimeter edging 36 which defines a viewer opening 38 located at the upper front wall section 24a of viewer housing 20. The lower front wall section 24b includes a pair of exterior upper and lower holding compartments 40 and 42 in the configuration of U-shaped grooved channels for receiving and holding a counterfeit chemical detection pen 14 and a fluorescent marker pen 16, respectively. These pens 14 and 16 are used in conjunction with the counterfeit detection viewer apparatus 10 or with the counterfeit detection handset 60 to form a complete detection system for authenticating currency 12 and governmental documents. The upper and lower front wall sections 24a and 24b include a vertical U-shaped channel 56 for receiving the user's nose when peering into the viewer opening 38 during operational use. In addition, channel 56 extends through the pair of exterior upper and lower holding compartments 40 and 42, respectively, of lower front wall section 24b. Rear wall 26 includes a first circular opening 50 for receiving an exterior ON/OFF button 52. Sidewall 30 includes circular opening 54 for an AC electrical wire connector 84 being used in conjunction with an AC adaptor connector 86, as shown in FIGS. 4, 6 and 8.

The interior surface of internal compartment 44 is coated with a dark layer of material (for example, black) which provides a better contrast of illumination to the viewer when the UV fluorescent tube 94 is turned on and is in operational use. The housing unit 20 preferably has a width of 18.5 cm, a depth of 16.5 cm, and a height of 12 cm. The viewer opening 38 preferably has a width of 3.3 cm and length of 12 cm. Housing 20 may be made of a moldable and durable plastic or a lightweight metal material.

Figure 7:
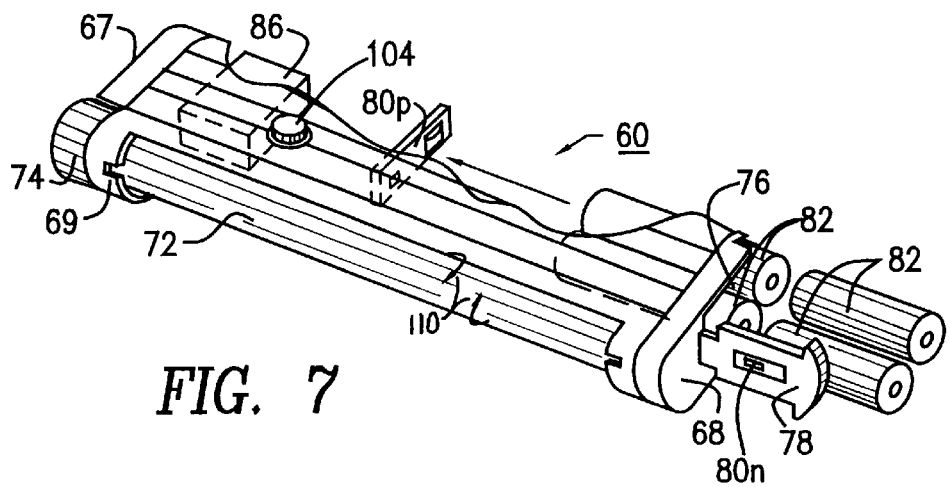
FIG. 7 is a rear perspective view of the counterfeit detection viewer apparatus of the present invention showing the removable portable counterfeit detector handset having the internal UV lighting assembly and its major component parts contained therein, and in a non-operational mode where the rotary cover is completely closed for protecting the UV fluorescent tube from breakage.
Figure 8:
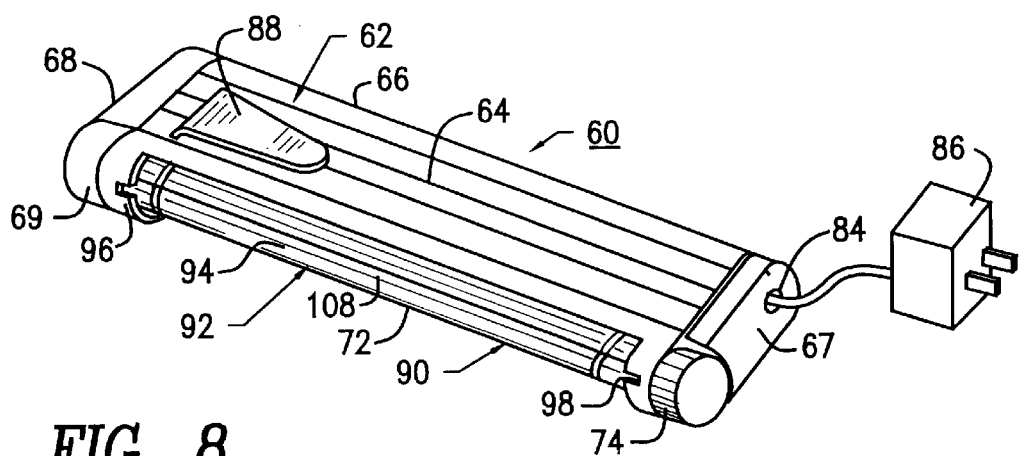
FIG. 8 is a front perspective view of the counterfeit detection viewer apparatus of the present invention showing the removable portable counterfeit detector handset having the internal UV lighting assembly and its major component parts contained therein, and in preparation for operational use where the rotary cover is completely opened for exposing the UV fluorescent tube for use within the viewer housing of the counterfeit detection viewer apparatus.
Figure 9:
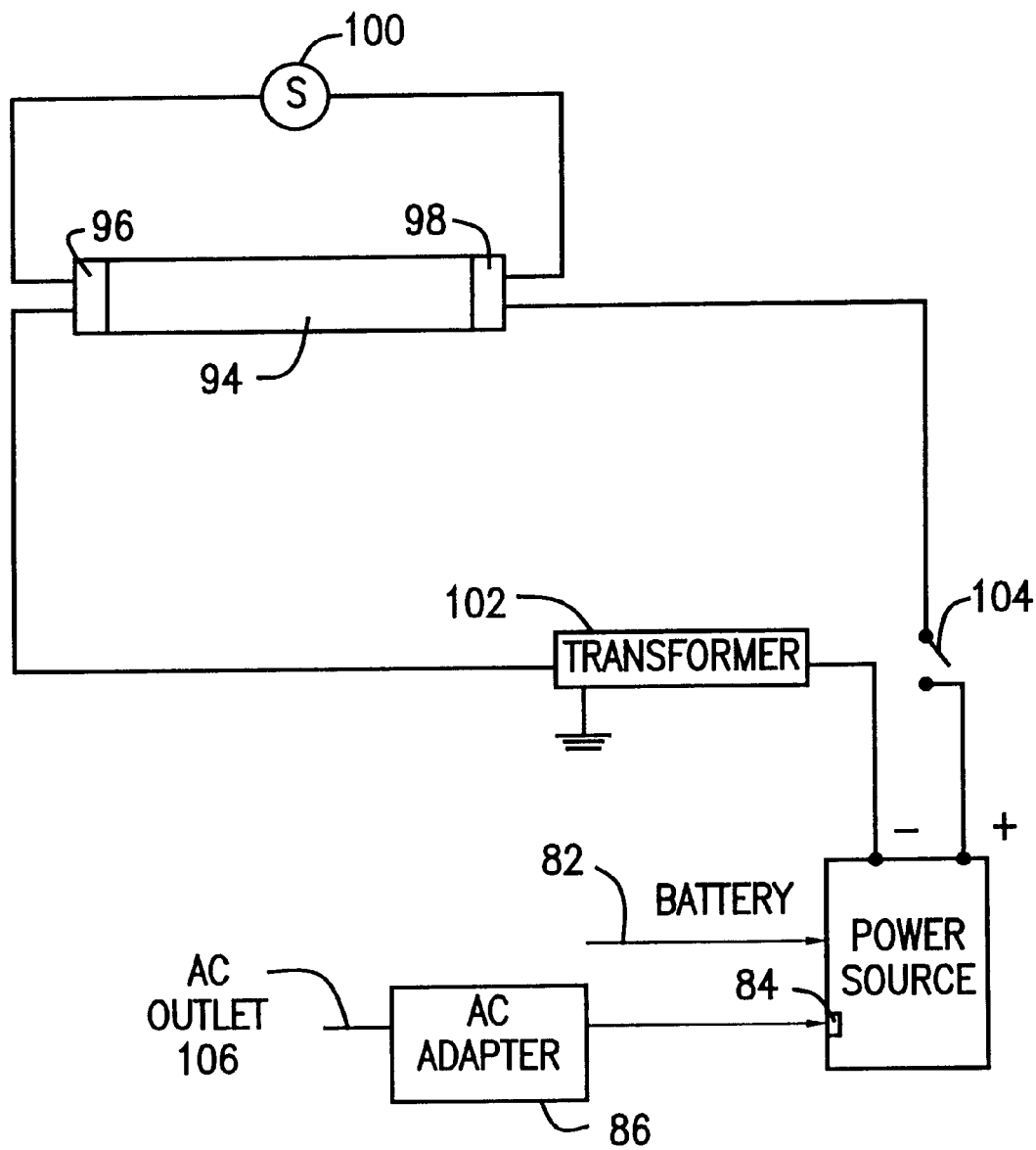
FIG. 9 is an electrical schematic diagram of the counterfeit detection viewer apparatus of the present invention showing the electrical circuit of the counterfeit detector handset.

The detachable and removable portable counterfeit detection handset or detector unit 60, as shown in FIGS. 2, and 6 to 8, includes a handset housing 62 having a front wall 64, a rear wall 65, a top wall 66, side walls 67 and 68, and a bottom wall 69. Counterfeit detector unit 60 further includes a compartment 70 located within the bottom wall 69 of handset housing 62 for receiving the UV lighting assembly 90 therein, and a black rotary cover 72 having a rotary knob 74 for turning and covering the UV fluorescent tube 94 when the handset 60 or the counterfeit detection viewer apparatus 10 is not in use. In addition, handset housing 62 includes an internal battery compartment 76 adjacent to the top wall 66 and having a slidable or movable battery cover 78 located on sidewall 68 of handset housing 62. The internal battery compartment 76 includes a positive pole (+) member 80p and a negative pole (-) member 80n for holding a plurality of batteries 82 therein. Battery compartment 76 also includes an AC electrical adaptor component 84 having an AC adaptor connector 86 being adjacent to the aforementioned battery compartment 76, as depicted in FIGS. 2, 7 and 9 of the drawings. The rear wall 65 of handset housing 62 includes an opening 120 for an ON/OFF button 104. Opening 120 of handset housing 62 is in alignment with opening 50 of viewer housing 20, such that when the handset detector unit 60 is attached to the viewer housing 20, respectively, of counterfeit detection viewer apparatus 10, as shown in FIGS. 4 and 5 of the drawings, ON/OFF buttons 104 and 52 are also aligned and are adjacent to each other. When the user depresses the exterior ON/OFF button 52 it in turn depresses the ON/OFF button 104 of hand-held detector unit 60 to turn the UV fluorescent light tube 94 ON or OFF accordingly. In addition, when the rotary knob 74 is turned and rotated such that rotary cover 72 is completely in a closed position 110, the UV fluorescent tube 94 will be turned off. Front wall 64 includes a carrying clip 88, as shown in FIG. 8 of the drawings. Handset housing 62 of the counterfeit detector unit 60 may be made of a moldable and durable plastic or a lightweight metal material.

The internal UV lighting assembly 90, as shown in FIGS. 2 to 5, 7, and 9 of the drawings, includes a UV lighting fixture 92 having a UV fluorescent tube 94 which is received within miniature sockets 96 and 98. The UV lighting assembly 90 further includes a UV starter 100, a UV transformer 102, an ON/OFF switch or button 104 for batteries 82 or the AC adaptor component 84 for being connected to an AC outlet 106. The UV fluorescent tube 94 has a length in the range of 6 cm to 18 cm with a preferred length of 11 cm. Also, the UV fluorescent tube 94 has a power rating specification in the range of 2 watts to 6 watts with a preferred power rating of 3 watts.

The distance between the UV fluorescent tube 94 and the currency bill 12 being scanned should not be more than 0.5 centimeters (cm), as this small distance between the UV fluorescent tube 94 and bill 12 also provides a more intense illumination of the security marking 18 being scanned when the counterfeit detector unit 60 is attached within viewer housing 20. For example, the new U.S. $100 dollar bills 12 have a security thread marking 18 which glows red under the intense illumination provided by the UV fluorescent tube 94 of the UV lighting fixture 92 within the viewer apparatus 10. Also, the new U.S. $50 dollar bills 12 have a security thread marking 18 which glows yellow under the intense illumination provided by the UV fluorescent tube 94 of the UV fixture 92 within the viewer apparatus 10. Currency bills 12 (for example, the U.S. $100 and $50 bill) not having the red glow or yellow glow of the security thread marking 18 indicates that currency bill 12 being tested is a counterfeit. Genuine currency bills 12 will not reflect the UV light from the UV fluorescent tube 94, whereas forged or counterfeit bills will become fluorescent and the counterfeit paper becomes a bright blue.

The user could also do a duplicate check by using the counterfeit chemical detection pen 14 from compartment 40 which would also show the authenticity or the invalidity of the currency bill 12 being tested by the user.

In addition, viewer apparatus 10 or handset detector unit 60 uses a UV starter 100 and a UV transformer 102 to light-up the UV fluorescent tube 94 via ON/OFF button 104, as shown in FIGS. 7 and 9. Further, when the black rotary cover 72 is completely closed via rotary knob 74 (rotation of cover is 100%), the cover 72 also acts as a disconnect to the plurality of batteries 82 when the viewer apparatus 10 or handset detector unit 60 is not in operational use by the user; and cover 72 also protects the UV fluorescent tube 94 from breakage.

OPERATION OF THE PRESENT INVENTION

In operation, the user places the detection opening 34 of the counterfeit detection viewer apparatus 10 having the counterfeit detector unit 60 attached therein, over the paper currency bill 12 to be inspected and scanned, as depicted in detail by FIG. 3. For example, new U.S. currency bills have included a polymer thread with fluorescent markings sensitive to UV fluorescent light; and which will glow red for U.S. $100 dollar bills or glow yellow for U.S. $50 dollar bills depending upon the denomination of the currency bill 12 being scanned under the intense UV fluorescent illumination. Next, the user rotates and completely opens the black rotary cover 72 via rotary knob 74 to a fully opened position 108 to expose UV fluorescent tube 94. The user then depresses the exterior ON/OFF button 52 to the ON position which in turn activates and illuminates the UV fluorescent tube 94 via the power source of batteries 82 of the UV lighting assembly 90. The user then peers into the viewer opening 38 in order to determine the validity and authenticity of the currency bill 12 being scrutinized. The new U.S.

$100 and $50 dollar bills 12 have a security thread marking 18 within the bill 12 which glows red or yellow, respectively, under the intense illumination provided by the UV fluorescent tube 94 of the UV fixture 92 of the viewer apparatus 10. The viewer will instantly see if a security marking 18 is present on the bill 12 being scanned as is it will glow red or yellow and if there is no security marking 18 on the bill 12 being scanned, then the bill 12 is determined to be a counterfeit. Genuine currency bills 12 will not reflect the UV light from the UV fluorescent tube 94, whereas forged or counterfeit bills will become fluorescent and the counterfeit paper becomes a bright blue. An additional check can be used to determine authenticity or invalidity of bill 12 by the use of the counterfeit chemical detection pen 14. The use of the viewer apparatus 10 and detection pen 14 provides an effective counterfeit detection system for determining if paper currency 12 is counterfeit. When the user has finished operating the counterfeit detection viewer apparatus 10, the user simply depresses again the ON/OFF button 52 to shut off the viewer apparatus 10. This conserves and saves the life of the batteries 82 being used to energize the viewer apparatus 10. Also, when the user completely rotates and closes the black rotary cover 72 to a fully closed position 110 via rotary knob 74, the viewer apparatus 10 will also be in a non-operational mode.

When the user removably detaches the counterfeit detector unit 60 from the housing unit 20 of viewer apparatus 10, the user can now scan and inspect the paper currency bill 12, as shown in FIG. 6 of the drawings, in any dark room or dark area of the user's choice without the viewer housing 20. A dark room or dark area is defined as a room or area where ambient light is not present when the detector unit 60 is being used. The user then proceeds to partially rotate and open the black rotary cover 72 to a halfway opened position 112 via rotary knob 74 in order to partially expose the UV fluorescent tube 94 on the counterfeit detector unit 60. The halfway rotated cover 72, as shown in FIG. 6, becomes a shield protecting the lower half of the UV fluorescent tube 94 from ambient light. The user then depresses the ON/OFF button 104 to the ON position which in turn activates and illuminates the UV fluorescent tube 94 via the power source of batteries 82 of the UV lighting assembly 90. The user then scans and inspects the paper currency bill 12 in the dark room or dark area via the partially exposed UV fluorescent tube 94 in order to determine the validity and authenticity of the currency bill 12 being scrutinized. As previously described, the viewer will instantly see if a security marking 18 is present on the bill 12 being scanned as is it will glow red or yellow and if there is no security marking 18 on the bill 12 being scanned, then the bill 12 is determined to be a counterfeit. Genuine currency bills 12 will not reflect the UV light from the UV fluorescent tube 94, whereas forged or counterfeit bill will become fluorescent and the counterfeit paper becomes a bright blue. An additional check can be used to determine authenticity or invalidity of bill 12 by the use of the counterfeit chemical detection pen 14. The use of the hand-held counterfeit detector unit 60 and detection pen 14 provides an effective counterfeit detection system for determining if paper currency 12 is counterfeit. When the user has finished operating the hand-held counterfeit detector unit 60, the user simply depresses again the ON/OFF button 104 to shut off the detector unit 60. This conserves and saves the life of the batteries 82 being used to energize the counterfeit detector unit 60. Also, when the user completely rotates and closes the black rotary cover 72 to a fully closed position 110 via rotary knob 74 on the hand-held counterfeit detector unit 60, the detector unit 60 will also be in a non-operational mode, as shown in FIG. 7 of the drawings.

ADVANTAGES OF THE PRESENT INVENTION

Accordingly, an advantage of the present invention is that it provides for a counterfeit detection viewer apparatus that allows for instantaneous detection of security markings of valid and authentic paper currency, or showing the lack of proper security markings of a counterfeit paper currency.

Another advantage of the present invention is that is provides for a counterfeit detection viewer apparatus for instantly detecting the security markings and verifying the validity and authenticity of any essential documents that include passports, entry visas, immigration green cards, driving licenses, vehicle registrations, credit cards, travelers checks, or other foreign currencies.

Another advantage of the present invention is that it provides for a counterfeit detection viewer apparatus for instantly detecting counterfeit paper currency by providing a housing to intensify UV fluorescent light rays from a fluorescent lamp, even under normal ambient bright lighting conditions.

Another advantage of the present invention is that it provides for a counterfeit detection viewer apparatus having a detachable counterfeit detector hand-held unit that is easy to use, portable, convenient and durable.

Another advantage of the present invention is that it provides for a counterfeit detection viewer apparatus having a detachable counterfeit detector unit that is portable, battery-operated, lightweight, compact and hand-held.

Another advantage of the present invention is that it provides for a detachable counterfeit detector unit having a black rotary cover that can be turned and rotated halfway over to become a shield protecting the lower half of the UV fluorescence tube from ambient light during operational use.

Another advantage of the present invention is that it provides for a detachable counterfeit detector unit having a black rotary cover, such that when the cover is completely closed (100% rotation), the cover will disconnect the batteries and will also protect the UV fluorescent tube from breakage when the detachable counterfeit detector unit is carried in a user's pocket, purse, knap-sack, carrying case or attache case.

Another advantage of the present invention is that it provides for a counterfeit detection viewer apparatus having exterior storage compartments for pen-type chemical markers that include a counterfeit chemical detector counterfeit paper currency and a fluorescent marker for identification of valuables under UV lighting.

A further advantage of the present invention is that it provides for a counterfeit detection viewer apparatus that can be mass produced in an automated and economical manner and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A counterfeit detection viewer apparatus for detecting security markings in paper currency, comprising:

a) a viewer housing having a detection opening on the bottom thereof for receiving the paper currency to be inspected and a viewing opening on the top thereof for inspecting the paper currency;

b) said viewer housing including means for removably mounting a hand-held counterfeit detector unit within said viewer housing for use as part of said viewer housing or as an independent hand-held counterfeit detector unit in a dark area;

c) said counterfeit detector unit including a UV light fixture mounted in said counterfeit detector unit having a UV fluorescent lamp for projecting UV light rays toward said detection opening and the paper currency to be inspected; said UV fluorescent lamp being less than 0.5 cm from said detection opening;

d) said counterfeit detector unit having a movable cover for protecting said UV fluorescent lamp when not in use;

e) said counterfeit detector unit including a battery compartment for receiving batteries to power said UV fluorescent lamp; and f) means for activating said UV fluorescent lamp prior to inspecting the paper currency through said viewing opening.

2. A counterfeit detection viewer apparatus in accordance with claim 1, wherein said means for removably mounting said hand-held counterfeit detector unit includes a pair of holding brackets mounted within said viewer housing for detachably holding in place said counterfeit detector unit.

3. A counterfeit detection viewer apparatus in accordance with claim 1, wherein said movable cover is a black rotary cover.

4. A counterfeit detection viewer apparatus in accordance with claim 1, wherein said movable cover includes means in a fully closed position for inactivating said UV fluorescent lamp.

5. A counterfeit detection viewer apparatus in accordance with claim 1, wherein said means for activating includes a switch located on said counterfeit detector unit.

6. A counterfeit detection viewer apparatus in accordance with claim 5, wherein said means for activating said UV fluorescent lamp includes a battery compartment having a plurality of batteries for generating electrical current.

7. A counterfeit detection viewer apparatus in accordance with claim 5, wherein said switch extends through said viewer housing for activation by the user.

8. A counterfeit detection viewer apparatus in accordance with claim 1, wherein said viewer housing has an exterior wall, said exterior wall having recesses formed therein for receiving counterfeit detector pens.

9. A counterfeit detection viewer apparatus in accordance with claim 1, wherein said viewer housing is made of a plastic or a lightweight metal.

10. A counterfeit detection viewer apparatus in accordance with claim 1, wherein said counterfeit detector unit is made of a plastic or a light-weight metal.

11. A counterfeit detection viewer apparatus in accordance with claim 1, wherein said UV fluorescent lamp has a length in the range of 6 cm to 18 cm.

12. A counterfeit detection viewer apparatus in accordance with claim 1, wherein said UV fluorescent lamp has a power rating specification in the range of 2 watts to 6 watts.

13. A counterfeit detection viewer apparatus in accordance with claim 1, wherein said UV fluorescent lamp has a length of 11 cm.

14. A counterfeit detection viewer apparatus in accordance with claim 1, wherein said UV fluorescent lamp has a power rating specification of 4 watts.

15. A hand-held counterfeit detector unit for detecting security markings in paper currency, comprising;

a) a hand-held housing having means for removably mounting said hand-held counterfeit detector unit inside a viewer housing so that said hand-held counterfeit detector unit may be used in combination with said viewer housing or may be used independently of said viewer housing in a dark area;

b) said counterfeit detector unit including a UV light fixture mounted in said counterfeit detector unit having a UV fluorescent lamp for projecting UV light rays toward the paper currency to be inspected;

c) said counterfeit detector unit having a movable cover for protecting said UV fluorescent lamp when not in use;

d) said counterfeit detector unit including a battery compartment for receiving batteries to power said UV fluorescent lamp; and e) means for activating said UV fluorescent lamp prior to inspecting the paper currency through said viewing opening.

16. A hand-held counterfeit detector unit in accordance with claim 15, wherein said means for removably mounting said hand-held counterfeit detector unit includes a pair of side walls shaped to be received in holding brackets mounted within said viewer housing for detachably holding in place said counterfeit detector unit.

17. A hand-held counterfeit detector unit in accordance with claim 15, wherein said movable cover is a black rotary cover.

18. A hand-held counterfeit detector unit in accordance with claim 15, wherein said movable cover includes means in a fully closed position for inactivating said UV fluorescent lamp.

19. A hand-held counterfeit detector unit in accordance with claim 15, wherein said means for activating includes a switch located on said counterfeit detector unit.

20. A hand-held counterfeit detector unit in accordance with claim 19, wherein said switch extends through said housing for activation by the user.

21. A hand-held counterfeit detector unit in accordance with claim 15, wherein said means for activating said UV fluorescent lamp includes a battery compartment having a plurality of batteries for generating electrical current.

22. A hand-held counterfeit detector unit in accordance with claim 15, wherein said counterfeit detector unit is made of a plastic or a light-weight metal.

23. A hand-held counterfeit detector unit in accordance with claim 15, wherein said UV fluorescent lamp has a length in the range of 6 cm to 18 cm.

24. A hand-held counterfeit detector unit in accordance with claim 15, wherein said UV fluorescent lamp has a power rating specification in the range of 2 watts to 6 watts.

25. A hand-held counterfeit detector unit in accordance with claim 15, wherein said UV fluorescent lamp has a length of 11 cm.

26. A hand-held counterfeit detector unit in accordance with claim 15, wherein said UV fluorescent lamp has a power rating specification of 4 watts.

27. A hand-held counterfeit detector unit for detecting security markings in paper currency, comprising;

a) a hand-held housing having means for removably mounting said hand-held counterfeit detector unit inside a viewer housing so that said hand-held counterfeit detector unit may be used in combination with said viewer housing or may be used independently of said viewer housing in a dark area;

b) said counterfeit detector unit including a UV light fixture mounted in said counterfeit detector unit having a UV fluorescent lamp for projecting UV light rays toward the paper currency to be inspected;

c) said counterfeit detector unit including a battery compartment for receiving batteries to power said UV fluorescent lamp; and d) means for activating said UV fluorescent lamp prior to inspecting the paper currency through said viewing opening.

28. A hand-held counterfeit detector unit for detecting security markings in paper currency, comprising;

a) a hand-held housing having means for removably mounting said hand-held counterfeit detector unit inside a viewer housing so that said hand-held counterfeit detector unit may be used in combination with said viewer housing or may be used independently of said viewer housing in a dark area;

b) said counterfeit detector unit including a UV light fixture mounted in said counterfeit detector unit having a UV fluorescent lamp for projecting UV light rays toward the paper currency to be inspected;

c) said counterfeit detector unit including a battery compartment for receiving batteries to power said UV fluorescent lamp;

d) said counterfeit detector unit including an adaptor connector for connection to a power source for supplying power to said UV fluorescent lamp; and e) means for activating said UV fluorescent lamp prior to inspecting the paper currency through said viewing opening.

29. A hand-held counterfeit detector unit in accordance with claim 28, wherein said adaptor connector is an AC adaptor for connection to an AC outlet.

30. A hand-held counterfeit detector unit in accordance with claim 28, wherein said adaptor connector is a DC adaptor for connection to a DC source of power.

* * * * *